United States Patent [19]

Suzuki

[11] 4,188,494
[45] Feb. 12, 1980

[54] HYDROGEN FLUORIDE REMOVAL FROM GLYCOLIC ACID

[75] Inventor: Shigeto Suzuki, San Francisco, Calif.

[73] Assignee: Chevron Research Company, San Francisco, Calif.

[21] Appl. No.: 931,333

[22] Filed: Aug. 7, 1978

Related U.S. Application Data

[63] Continuation-in-part of Ser. No. 790,221, Apr. 25, 1977, abandoned.

[51] Int. Cl.$^2$ ............................................. C07C 59/06
[52] U.S. Cl. .................................... 562/580; 560/179
[58] Field of Search ......................... 560/179; 562/580

[56] References Cited

U.S. PATENT DOCUMENTS

| | | | |
|---|---|---|---|
| 3,911,003 | 10/1975 | Suzuki | 560/179 |
| 3,962,343 | 6/1976 | Fujiyama et al. | 260/599 |

OTHER PUBLICATIONS

Kirk-Othmer, "Encyclopedia of Chemical Technology", 2nd ed., 1966, vol. 9, p. 617.
Mahin, Edward G., "Quantitative Analysis", McGraw Hill Publ., (1924), pp. 25–28.
Lundell, G. E. F. et al., "Applied Inorganic Analysis", 2nd Ed., (1953), John Wiley & Sons Publ., at p. 102.

*Primary Examiner*—Bernard Helfin
*Assistant Examiner*—L. Hendriksen
*Attorney, Agent, or Firm*—D. A. Newell; John Stoner, Jr.; A. T. Bertolli

[57] ABSTRACT

The concentration of hydrogen fluoride in crude glycolic acid made by the hydrogen fluoride-catalyzed reaction of formaldehyde and carbon monoxide can be reduced to less than about 1% by weight by removing the HF from the crude gylcolic acid by distillation or stripping with inert gas at a temperature above about 130° C., thereby producing a polyglycolide subsequently convertible to glycolic acid by hydrolysis.

4 Claims, 1 Drawing Figure

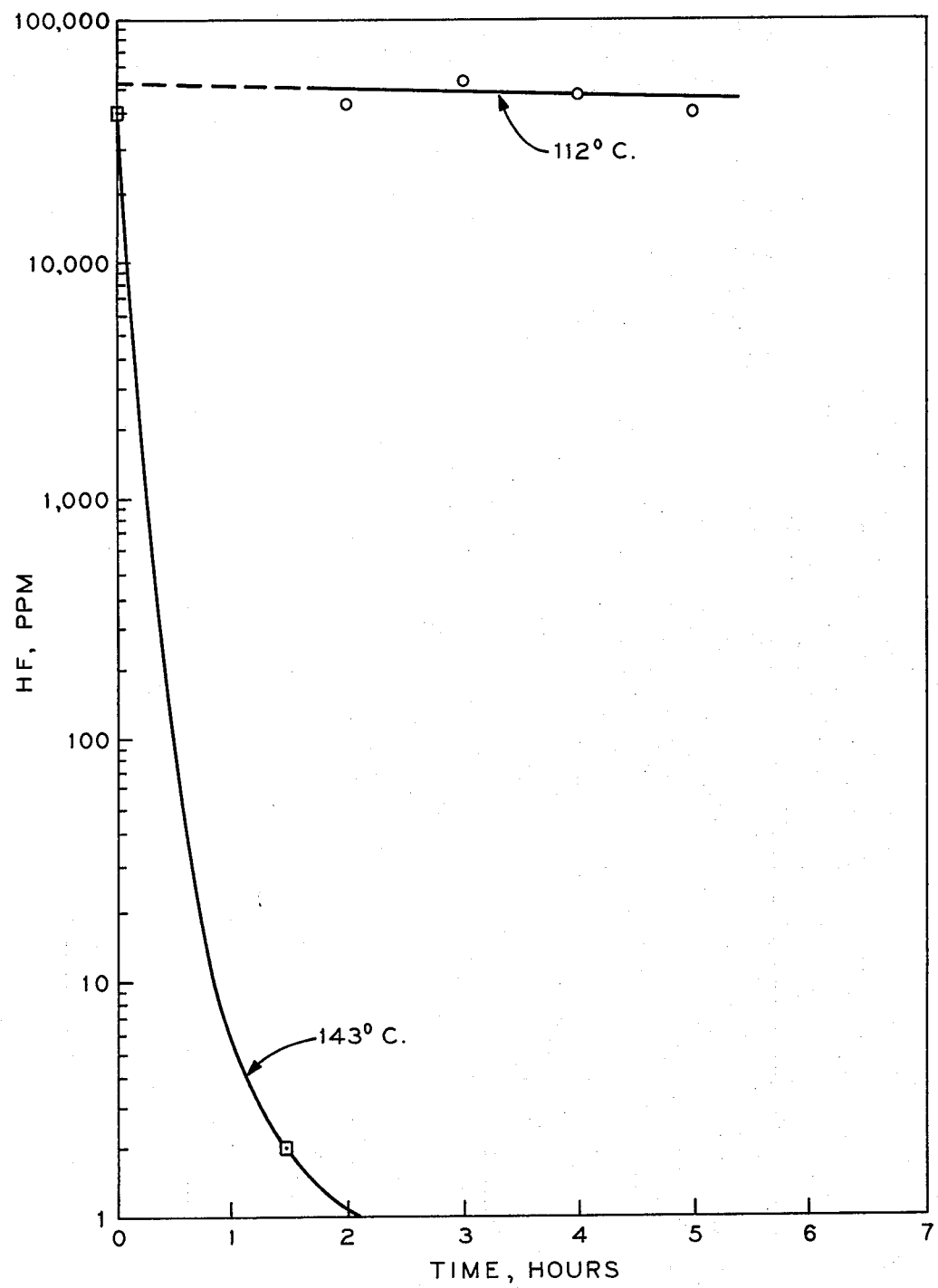

500
HYDROGEN FLUORIDE REMOVAL FROM GLYCOLIC ACID

CROSS-REFERENCE TO RELATED APPLICATIONS

This application is a continuation-in-part of U.S. application Ser. No. 790,221, filed Apr. 25, 1977 now abandoned.

BACKGROUND OF THE INVENTION

This invention concerns an improved process for removing hydrogen fluoride from glycolic acid.

Recently hydrogen fluoride has been found to be a surprisingly effective catalyst for glycolic acid production. For instance, U.S. Pat. No. 3,911,003, granted Oct. 7, 1975, describes a process for preparing glycolic acid by contacting formaldehyde, carbon monoxide and water in the presence of a hydrogen fluoride catalyst. For economy of process and for subsequent processing of the crude product, it is necessary to separate the hydrogen fluoride catalyst from the crude glycolic acid product. It is usually necessary to reduce the hydrogen fluoride content of the product to a few parts per million, or even to less than one part per million, before the product can be used. It would be expected that, as hydrogen fluoride is quite volatile, it would readily be removed by distillation or by stripping with inert gas at moderate temperatures. For example, U.S. Pat. No. 2,534,017 shows that hydrogen fluoride can readily be removed from aromatic aldehydes by vacuum distillation at 55° C. to 85° C.; and U.S. Pat. No. 3,962,343 shows rapid removal of hydrogen fluoride in a similar system by stripping with a hydrocarbon diluent or by decomposing in a film-evaporator at 80° C. to 110° C. It has been found, in agreement with this, that most of the hydrogen fluoride can be removed from the crude glycolic acid-hydrogen fluoride product formed by the process of U.S. Pat. No. 3,911,003 by distilling or stripping with gas at temperatures at or below 110° C. However, when the concentration of hydrogen fluoride in crude glycolic acid has been reduced to about 4% by weight, i.e., about 40,000 ppm, further stripping with an inert gas or distillation at these temperatures does not significantly reduce the hydrogen fluoride concentration.

Accordingly, in order to obtain a glycolic acid product having less than about 4%, by weight, of hydrogen fluoride, an improved process is desirable. Hydrogen fluoride is an unwanted contaminant because of its corrosive and toxic nature, and hence the production of a hydrogen fluoride-free glycolic acid for use in later processing is most beneficial, for example, where the glycolic acid may be used in the preparation of high-molecular-weight suture-grade polyglycolides suitable for human application.

SUMMARY OF THE INVENTION

It has been found that the concentration of hydrogen fluoride in crude glycolic acid may be reduced to less than about 0.1% by weight by heating the crude glycolic acid to a temperature of at least about 130° C. during the removal, or purification step, thereby producing a low-molecular-weight glycolide, subsequently hydrolyzable to pure glycolic acid relatively free of hydrogen fluoride.

BRIEF DESCRIPTION OF THE DRAWING

The FIGURE compares the purification of crude glycolic acid by hydrogen fluoride stripping at a continuous temperature of about 110° C. to stripping at an increased temperature of about 140° C. Both runs were carried out at atmospheric pressure using nitrogen as an inert gas. As described in Example 1, stripping at 93° C. for over 8 hours did not reduce the hydrogen fluoride concentration below about 4%. In contrast, stripping at 110° C. for about 6 hours followed by only 1 hour of stripping at an increased temperature of about 140° C. reduced the hydrogen fluoride concentration to less than 2 ppm. Thus, while both temperatures were satisfactory for removing the bulk of the hydrogen fluoride, to obtain a useful product, for example one containing less than about 5 ppm of hydrogen fluoride, purification had to be carried out at a temperature in excess of about 130° C., preferably 140° C.

DETAILED DESCRIPTION OF THE INVENTION

This invention provides an improved process for purifying a crude glycolic reaction product. The term "crude glycolic acid" refers to the reaction product of the hydrogen-fluoride-catalyzed reaction of formaldehyde and carbon monoxide to form glycolic acid. This reaction is described in U.S. Pat. No 3,911,003. The crude product generally contains in excess of 40% by weight hydrogen fluoride.

While the purification of crude glycolic acid can be carried out in a variety of ways, the central feature of the invention is based on the discovery that, in order to reduce the hydrogen fluoride concentration to less than about 4%, the final stages of the removal of hydrogen fluoride must be carried out at a temperature in excess of about 130° C., preferably in excess of 140° C., up to about 160° C. The time required for this final stage of hydrogen fluoride removal can vary from 0.25 to 2.5 hours. For example, the time required for removal of 4% hydrogen fluoride at 143° C. was about 2 hours. Lower temperatures can be used during the initial stages to reduce the hydrogen fluoride content to about 4%, but the final reduction to less than about 4% requires a temperature in excess of about 130° C. Thus, the process comprises heating crude glycolic acid containing hydrogen fluoride to a temperature above about 90° C. until the concentration of hydrogen fluoride is about 4% by weight, and subsequently heating the crude product to a temperature in excess of about 130° C. If desired, the entire hydrogen-fluoride removal process can be conducted at temperatures above 130° C. In this way, the quantity of HF remaining in the product can be easily reduced to a value less than 100 ppm, preferably less than 10 ppm. Heating the crude reaction product in excess of 130° C., as aforesaid, produces low-molecular-weight polyglycolides (mainly dimers, trimers and tetramers) with concomitant loss of water. The polyglycolide is easily converted by hydrolysis with water to produce a pure glycolic acid. Conditions of hydrolysis are not critical, and temperatures between about 70°–100° C. can be used. If desired, hydrolysis may be effected at elevated temperatures at superatmospheric pressures, as is well known in the art. Following hydrolysis, pure glycolic acid can be recovered by cooling the aqueous solution to effect crystallization. Glycolic acid crystals are then obtained by filtration or by centrifugation. Or, if desired, the glycolic acid may be recovered as an aqueous solution, for example, as a 65% aqueous solution, consistent with conventional commercial practice.

The physical removal of hydrogen fluoride can be done by any known method. One method is to distill off the hydrogen fluoride at reduced pressure in a still or an evaporator. Another method of removing hydrogen fluoride is to pass an inert gas through the crude product, thereby stripping out the hydrogen fluoride.

Inert gas stripping and distillation are well-known methods of refining crude organic products. In general, inert gas stripping is carried out by passing an inert gas through a liquid mixture at a given temperature and pressure which are known to effect transfer of a volatile liquid component into the inert gas. In this way, a refined product having a reduced concentration of the transferred liquid is obtained. A thorough discussion of gas-stripping principles is contained in Perry's Chemical Engineers' Handbook 4th, Chapter 14.

The inability to remove hydrogen fluoride by continuous purification at temperatures of about 110° C. is apparently due to solvent differences at these temperatures. The vapor pressure of pure hydrogen fluoride is only twice as high at about 150° C. as at about 100° C.; so, if the solvent were unchanged, hydrogen fluoride removal would be only twice as fast at 150° C. as at 100° C. At the lower temperature, the solvent is mainly glycolic acid. The 4% weight hydrogen fluoride retained in the solution corresponds to about 1 mol of hydrogen fluoride for every 6 mols of glycolic acid. A strong acid such as hydrogen fluoride would be expected to be solvated by 4–8 mols of a hydroxylic solvent. Thus, it is believed that the surprising increase in reduction of hydrogen fluoride content which can be obtained by purification at a temperature in excess of about 140° C. is due to the tendency of glycolic acid to form polyglycolides. Apparently the conversion of glycolic acid to polyglycolide at about 140° C. not only decreases the content of free hydroxyl and carboxyl groups, but also forms solvent molecules which are too bulky to permit solvating protons with a large number of hydroxyl groups. This change in solvent properties then results in a greatly increased volatility for hydrogen fluoride. As a result, continuous stripping or distillation at about 110° C. will not remove the last 4% of the hydrogen fluoride, while an increase in temperature to about 130° C., preferably about 140° C., causes an almost logarithmic reduction with time. This suggests that the hydrogen fluoride vapor pressure at temperatures above about 140° C. is essentially proportional to the hydrogen fluoride concentration in the solution.

In a preferred embodiment of the invention, purification of crude glycolic acid is carried out by inert gas stripping using synthesis gas or carbon monoxide-depleted synthesis gas as the inert gas. As thoroughly described in U.S. Pat. No. 3,911,033, crude glycolic acid is prepared by the reaction of formaldehyde and carbon monoxide in the presence of a hydrogen fluoride catalyst. A preferred source of carbon monoxide in that process is synthesis gas comprising carbon monoxide and hydrogen. This synthesis gas can also act as a source of inert gas for the purification step. Alternatively, the carbon monoxide-depleted synthesis gas which is recovered after the reaction of carbon monoxide with formaldehyde to form glycolic acid can be used as a source of inert gas for the purification step.

The following examples further illustrates practice of the present invention.

EXAMPLE 1

In the following example, crude glycolic acid containing about 40% by weight hydrogen fluoride was subjected to nitrogen stripping for about 2 hours at 23° C. to 93° C. and then for about 6 hours at 93° C. to prepare a product containing 4.3% weight hydrogen fluoride. Stripping for 5 additional hours at 112° C. removed only a minor amount of the hydrogen fluoride from this mixture. However, after stripping the mixture for 1.5 additional hours at 143° C., the hydrogen fluoride content of the product decreased to about 2 ppm. Further gas stripping at 143° C. reduced the hydrogen fluoride content of the product to 0.1–0.2 ppm of hydrogen fluoride. These results are plotted in the FIGURE. The FIGURE is a plot of the percent hydrogen fluoride remaining in the reaction mixture after nitrogen stripping for a given number of hours at either 112° C. or 143° C. The plot is on a log scale in order to cover the entire concentration range of 1 ppm to 5% (50,000 ppm). As seen from the FIGURE, the influence of temperature on crude glycolic acid purification is extremely significant.

EXAMPLE 2

Three hundred eighty-eight parts, by weight, of a crude glycolic acid hydrogen fluoride product formed by the process of U.S. Pat. No. 3,911,003 was charged to a stainless steel stirred autoclave. Hydrogen fluoride and water were removed under the varying conditions tabulated below:

| Run No. | Time, Min. | Temp., °F. | Pressure | $N_2$,[4] SCFH | % F | Degree of Polym.[3] | Recovery, % HF | Recovery, % $H_2O$ |
|---|---|---|---|---|---|---|---|---|
| 1 | 200 | 150 | 1 Atm. | 5 |  | 1 | 68 | 12 |
| 2 | 160 | 180 | 1 Atm. | 5 |  | 1 | 86 | 32 |
| 3 | 90 | 200 | 1 Atm. | 5 |  | 1.3 | 96 | 33 |
| 4 | 80 | 300 | 1 Atm. | 5 |  | 1.5 | 97 | 50 |
| 5 | 45 | 150 | 1 Atm. | 0 |  | 3 | 67 | 25 |
| 6 | 78 | 300 | 1 Atm. | 0 | 0.4 | 1 | 99.7 | 35 |
| 7 | 73 | 150 | 25 mm | 0 | 0.4 | — | 99.7 | — |
| 8 | 70 | 300 | 25 mm | 0 | 0.5 | — | 99.6 | — |
| 9[1] | 58 | 150 | 1 Atm. | 0 |  | 1.6 | 41 | 29 |
| 10 | 92 | 350 | 1 Atm. | 2 | 0.5 | 2 | 99.6 | 65 |
| 11 | 104 | 360 | 1 Atm. | 2 | 0.8 | 1.9 | 99.3 | 62 |
| 12 | 33 | 160 | 1 Atm. | 0 |  | 3.2 | 82 | 31 |
| 13 | 78 | 290 | 1 Atm. | 2 |  | 2.6 | 97 | 17 |
| 14 | 66 | 300 | 1 Atm. | 0 | 1.8 | 4.0 | 98.5 | 52 |
| 15 | 385 | 300 | 1 Atm. | 2 | 0.7 | — | 99.4 | — |
| 16 | 307 | 300 | 1 Atm. | 2 | 1.8 | 4.0 | 98.5 | 52 |
| 17[2] | 300 | 300 | 1 Atm. | 2 | 0.3 | — | 99.8 | — |

-continued

| Run No. | Time, Min. | Temp., °F. | Pressure | N$_2$,[4] SCFH | % F | Degree of Polym.[3] | Recovery, % HF | H$_2$O |
|---|---|---|---|---|---|---|---|---|
| 18 | 304 | 300 | 25 mm | 0 | 0.05 | — | 99.9 | — |
| 19 | 315 | 400 | 25 mm | 0 | 0.2 | — | 99.9 | — |

[1]Run 9, no stirring.
[2]Run 17, ethylene glycol added.
[3]Bottoms degree of polymerization is calculated from Karl Fischer analysis of water in the overhead product.
[4]Nitrogen stripping gas flow rate is given in Standard cubic feet per hour.

[5]HF Recovery = $\dfrac{\text{HF in Overhead Product}}{\text{HF in Feed}}$

H$_2$O Recovery = $\dfrac{\text{H}_2\text{O in Overhead Product}}{\text{H}_2\text{O in Feed}}$

EXAMPLE 3

A sample of hydrogen fluoride free bottoms produced by the process of Example 2, 100 parts, was mixed with water, 80 parts, and heated to give a clear solution (below 100° C.). Heating was continued for two hours with periodic additions of water to maintain the water level constant. At the end of this time, the quantity of water was adjusted to give a 65% aqueous glycolic acid solution.

EXAMPLE 4

An aqueous glycolic acid solution prepared in the manner of Example 3 is cooled to effect crystallization of the glycolic acid, and the resulting glycolic acid recovered by filtration.

What is claimed is:

1. In a process for the removal of hydrogen fluoride by inert gas stripping or distillation from a crude glycolic acid obtained by the hydrogen fluoride catalyzed reaction of formaldehyde and carbon monoxide, the improvement which comprises effecting said removal at a temperature in excesss of about 130° C. at atmospheric pressure to produce polyglycolide, thereafter hydrolyzing said polyglycolide and recovering pure glycolic acid.

2. A process according to claim 1 wherein hydrogen fluoride removal is carried out by gas stripping.

3. A process according to claim 1 wherein the hydrogen fluoride removal is carried out at a temperature of about 100° C. for a period of time sufficient to obtain a product having about 4% by weight hydrogen fluoride and subsequent hydrogen fluoride removal is carried out at a temperature of about 130° C. to 160° C.

4. A proces according to claim 1 wherein the purification is carried out by inert gas stripping using a mixture of carbon monoxide and hydrogen as the inert gas.

* * * * *